(12) United States Patent
Kovac et al.

(10) Patent No.: US 7,379,771 B2
(45) Date of Patent: May 27, 2008

(54) CONDUCTION BASED AUTOMATIC THERAPY SELECTION

(75) Inventors: Joseph Kovac, Cambridge, MA (US); Julie Thompson, Circle Pines, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 309 days.

(21) Appl. No.: 10/978,936

(22) Filed: Nov. 1, 2004

(65) Prior Publication Data

US 2006/0095084 A1    May 4, 2006

(51) Int. Cl.
*A61B 5/046* (2006.01)
*A61B 5/0464* (2006.01)

(52) U.S. Cl. .......................................... 607/4; 600/517
(58) Field of Classification Search ................ 607/4–5, 607/7, 9, 14–15, 25–26; 600/515–518, 521
See application file for complete search history.

(56) References Cited

U.S. PATENT DOCUMENTS

| | | | | |
|---|---|---|---|---|
| 3,829,766 A | * | 8/1974 | Herz ........................... | 600/517 |
| 4,184,493 A | * | 1/1980 | Langer et al. ................. | 607/5 |
| 4,202,340 A | * | 5/1980 | Langer et al. ................. | 607/5 |
| 4,475,551 A | * | 10/1984 | Langer et al. ................. | 607/5 |
| 5,010,887 A | * | 4/1991 | Thornander ................. | 600/509 |
| 5,184,615 A | | 2/1993 | Nappholz et al. | |
| 5,203,326 A | | 4/1993 | Collins | |
| 5,205,283 A | * | 4/1993 | Olson ............................. | 607/4 |
| 5,342,402 A | * | 8/1994 | Olson et al. .................... | 607/5 |
| 5,354,316 A | * | 10/1994 | Keimel ........................ | 607/15 |
| 5,379,776 A | | 1/1995 | Murphy et al. | |
| 5,556,419 A | * | 9/1996 | Jarverud et al. ............... | 607/9 |
| 5,788,717 A | | 8/1998 | Mann et al. | |
| 5,797,967 A | | 8/1998 | KenKnight | |
| 5,891,169 A | * | 4/1999 | Boheim et al. ................. | 607/4 |
| 5,978,700 A | * | 11/1999 | Nigam ....................... | 600/518 |
| 6,016,442 A | * | 1/2000 | Hsu et al. .................... | 600/518 |
| 6,035,232 A | * | 3/2000 | Thong et al. ................ | 600/510 |
| 6,058,326 A | | 5/2000 | Hess et al. | |
| 6,058,328 A | | 5/2000 | Levine et al. | |
| 6,192,273 B1 | | 2/2001 | Igel et al. | |
| 6,272,377 B1 | | 8/2001 | Sweeney et al. | |
| 6,345,199 B1 | * | 2/2002 | Thong ........................... | 607/5 |
| 6,400,982 B2 | | 6/2002 | Sweeney et al. | |

(Continued)

OTHER PUBLICATIONS

Kim, J., et al., "Post-Shock Recovery Monitoring for Tachyarrhythmia Discrimination", U.S. Appl. No. 10/746,857, filed Dec. 24, 2003, 34 Pages.

(Continued)

*Primary Examiner*—Carl Layno
*Assistant Examiner*—Jessica L. Reidel
(74) *Attorney, Agent, or Firm*—Schwegman, Lundberg & Woessner, P.A.

(57) ABSTRACT

A system comprising an implantable medical device includes a ventricular heart signal sensing circuit, a pacing therapy circuit, and a controller circuit coupled to the signal sensing circuit and the therapy circuit. The controller circuit is operable to detect a ventricular tachycardia heart rhythm from the cardiac signal, measure an amount of time the heart signal is one of inside or outside of an effective amplitude band, and initiate ATP therapy if the measured amount of time is less than a threshold amount of time.

41 Claims, 6 Drawing Sheets

U.S. PATENT DOCUMENTS

| | | |
|---|---|---|
| 6,400,986 B1 | 6/2002 | Sun et al. |
| 6,748,269 B2 | 6/2004 | Thompson et al. |
| 2002/0120306 A1 | 8/2002 | Zhu et al. |
| 2002/0143367 A1* | 10/2002 | Levine et al. .................. 607/9 |
| 2004/0030256 A1 | 2/2004 | Lin |
| 2004/0116981 A1* | 6/2004 | Mazar ........................ 607/60 |

OTHER PUBLICATIONS

Lin, Y., "Cardiac Rhythm Management Systems and Methods for Detecting or Validating Cardiac Beats in the Presence of Noise", U.S. Appl. No. 10/210,193, filed Jul. 31, 2002, 28 Pages.

Thompson, J., et al., "Algorithm for Discrimination of 1:1 Tachycardias", U.S. Appl. No. 10/862,779, filed Jun. 7, 2004, 33 Pages.

* cited by examiner

CONDUCTION BASED AUTOMATIC THERAPY SELECTION

TECHNICAL FIELD

The field generally relates to implantable medical devices and, in particular, but not by way of limitation, to a system and method for discriminating between ventricular arrhythmias that are pace-terminable and those that are non-pace terminable.

BACKGROUND

Implantable medical devices (IMDs) are devices designed to be implanted into a patient. Some examples of these devices include cardiac rhythm management devices such as implantable pacemakers and implantable cardioverter defibrillators (ICDs). The devices are used to treat patients using electrical therapy and to aid a physician or caregiver in patient diagnosis through internal monitoring of a patient's condition. The devices may include electrical leads in communication with sense amplifiers to monitor electrical heart activity within a patient, and often include sensors to monitor other internal patient parameters. Some IMDs are able to provide both anti-tachyarrhythmia pacing (ATP) and defibrillation shock therapy. When tachyarrhythmia is detected, the device may first try to convert the arrhythmia with ATP before resorting to high energy defibrillation. If conversion is successful, ATP spares the patient from the pain of a high energy defibrillation shock. However, tachyarrhythmia can quickly degenerate into a life threatening condition. Therefore, it is necessary to provide an appropriate therapy as quickly as possible.

SUMMARY

Systems and methods are provided for treating cardiac arrhythmia. One system example comprises an implantable medical device (IMD) that includes a ventricular heart signal sensing circuit, a pacing therapy circuit, and a controller circuit coupled to the signal sensing circuit and the therapy circuit. The controller circuit is operable to detect a ventricular tachycardia heart rhythm from the cardiac signal, measure an amount of time the heart signal is outside of an effective amplitude band, and initiate ATP therapy if the measured amount of time is less than a threshold amount of time.

One method example comprises monitoring an electrical signal representative of ventricular depolarization in a heart of a patient, detecting a ventricular tachycardia heart rhythm using the electrical signal, measuring an amount of time the electrical signal is outside of an effective amplitude band, and classifying the ventricular tachycardia heart rhythm using the measured amount of time.

This summary is intended to provide an overview of the subject matter of the present patent application. It is not intended to provide an exclusive or exhaustive explanation of the invention. The detailed description is included to provide further information about the subject matter of the present patent application.

DETAILED DESCRIPTION

In the following detailed description, reference is made to the accompanying drawings which form a part hereof, and specific embodiments in which the invention may be practiced are shown by way of illustration. It is to be understood that other embodiments may be used and structural or logical changes may be made without departing from the scope of the present invention.

The present application discusses, among other things, systems and methods for detecting ventricular tachyarrhythmia. Some implantable medical devices (IMDs) are cardiac rhythm management devices which are designed to detect ventricular tachyarrhythmia and to provide therapy to the patient upon detection. These IMDs, such as implantable cardioverter defibrillators (ICDs), treat tachyarrhythmia by delivering a high energy electrical shock to the heart. Other IMDs are able to provide anti-tachyarrhythmia pacing (ATP) therapy. ATP uses lower energy pacing to establish a regular rhythm in a heart. This allows the tachyarrhythmia to be converted to a normal heart rhythm without resorting to high energy defibrillation therapy that can be painful to the patient. Some IMDs are able to provide both ATP and defibrillation therapies. Providing painless therapy, such as ATP therapy, improves the patient's experience with an IMD as well as increasing the battery longevity of the devices. Because tachyarrhythmia can quickly lead to a life threatening condition, some physicians may be uncomfortable with the use of ATP because of the potential for delaying more effective shock therapy. Therefore, it is important to distinguish pace-terminable arrhythmias from non-pace-terminable arrhythmias.

Figure 1:
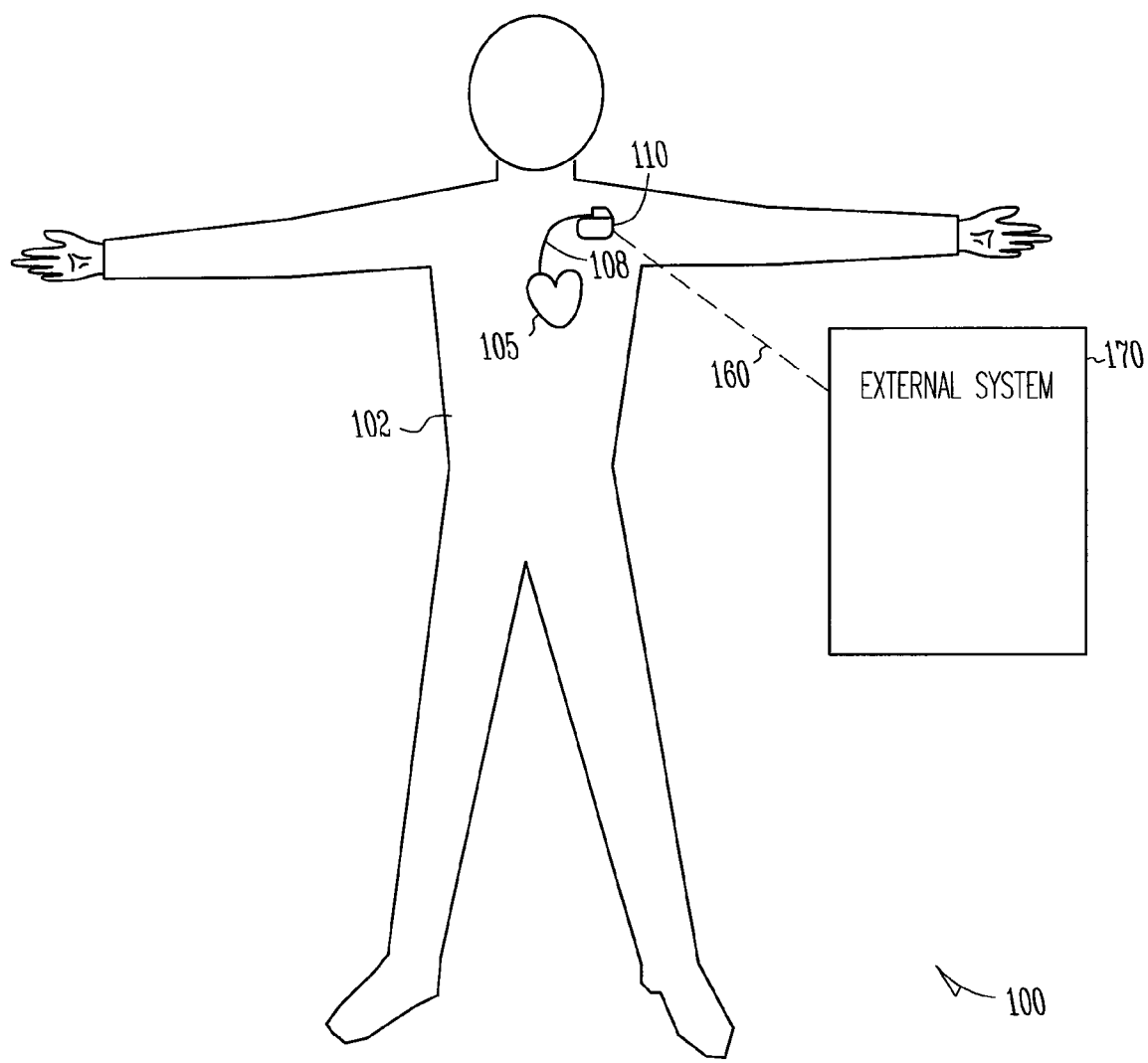
FIG. 1 illustrates an embodiment of a system that uses an implantable medical device.

FIG. 1 illustrates an embodiment of a system 100 that uses an implantable medical device (IMD) 110. The system 100 shown is one embodiment of portions of a system 100 used to treat a cardiac arrhythmia. A pulse generator (PG) or other IMD 110 is coupled by a cardiac lead 108, or additional leads, to a heart 105 of a patient 102. Examples of IMD 110 include, without limitation, a pacer, a defibrillator, a cardiac resynchronization therapy (CRT) device, or a combination of such devices. System 100 also includes an IMD programmer or other external system 170 that typically provides wireless communication signals 160 to communicate with the IMD 110, such as by using telemetry or radio frequency (RF) signals.

Cardiac lead 108 includes a proximal end that is coupled to IMD 110 and a distal end, coupled by an electrode or electrodes to one or more portions of a heart 105. The electrodes are for delivering atrial and/or ventricular cardioversion/defibrillation and/or pacing and/or resynchronization therapy to the heart 105. IMD 110 includes components that are enclosed in a hermetically-sealed canister or "can." Additional electrodes may be located on the can, or on an insulating header, or on other portions of IMD 110, for providing unipolar pacing and/or defibrillation energy in conjunction with the electrodes disposed on or around heart 105. The lead 108 or leads and electrodes are also used for sensing electrical activity of a heart 105. To determine how to recognize episodes of pace-terminable tachyarrhythmia, prior medical devices used heart rate or heart rate stability based measurements.

In the interest of advancing device technology, we analyzed a database containing the sensed electrical heart activity signals of several patients to determine if recognition of pace-terminable arrhythmias could be improved. The sensed signals, or waveforms, included episodes of arrhythmias that were converted to normal heart rhythms with ATP and episodes that were not converted with ATP. The analysis showed that morphology information extracted from the waveform can be used to predict whether a tachyarrhythmia is pace-terminable. Specifically, the analysis showed that the more time a signal waveform of a tachyarrhythmia spends near a signal baseline, the more likely that it is a pace-terminable tachyarrhythmia.

Figure 2:
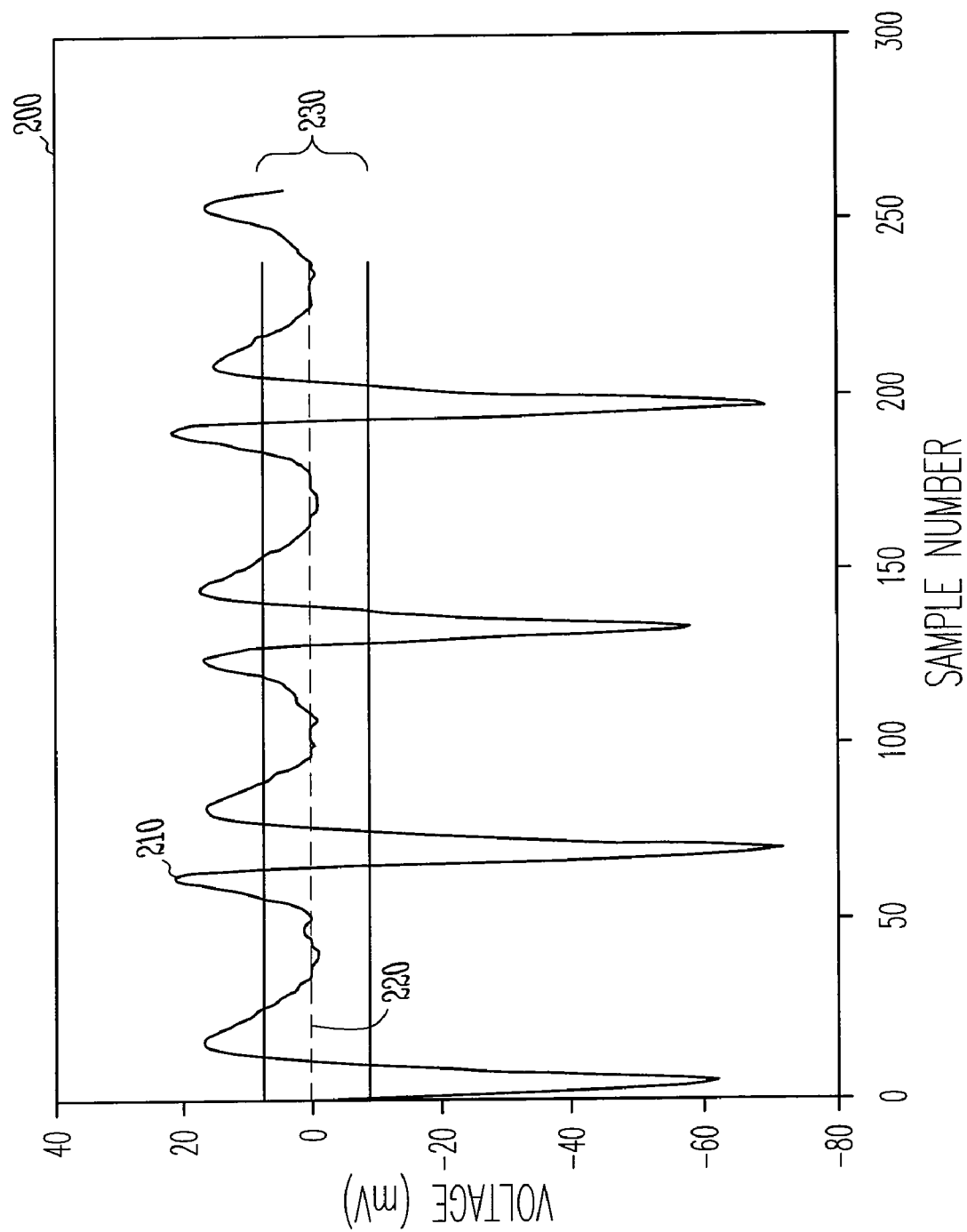
FIG. 2 is a graph showing a segment of a signal waveform of ventricular tachyarrhythmia that was successfully converted to a normal heart rhythm using ATP.

FIG. 2 is a graph 200 showing a segment of a signal waveform 210 of ventricular tachyarrhythmia that was successfully converted to a normal heart rhythm using ATP. The graph 200 shows voltage in millivolts (mV) as a function of sample number. In one example, a signal baseline 220 is defined as a hypothetical line drawn parallel to the x-axis (i.e. a line of DC voltage) that has the highest number of signal crossings through it. In the graph 200 shown, the signal baseline 220 value is about zero millivolts. Once the signal baseline 220 is identified or estimated, a signal amplitude band 230 around the signal baseline 220 is identified. In one embodiment, the effective amplitude band 230 has a width equal to a fraction or percentage of the signal waveform 210 amplitude and centered about the signal baseline 220. The effective amplitude is defined as a signal's maximum less its minimum averaged over a number of intervals. In one example, the width of the effective amplitude band 230 is set to about one-third of the signal waveform peak-to-peak amplitude averaged over four intervals. Other fractions and other measurements of amplitude, such as for example zero-to-peak, are within the scope of the method. A segment of the signal waveform 210 is then classified using an amount of time the waveform signal 210 spends outside of the band 230. Of course, classifying a signal waveform 210 based on an amount of time spent inside, rather than outside, the band 230 is only a logical change and is within the scope of the method.

Figure 3:
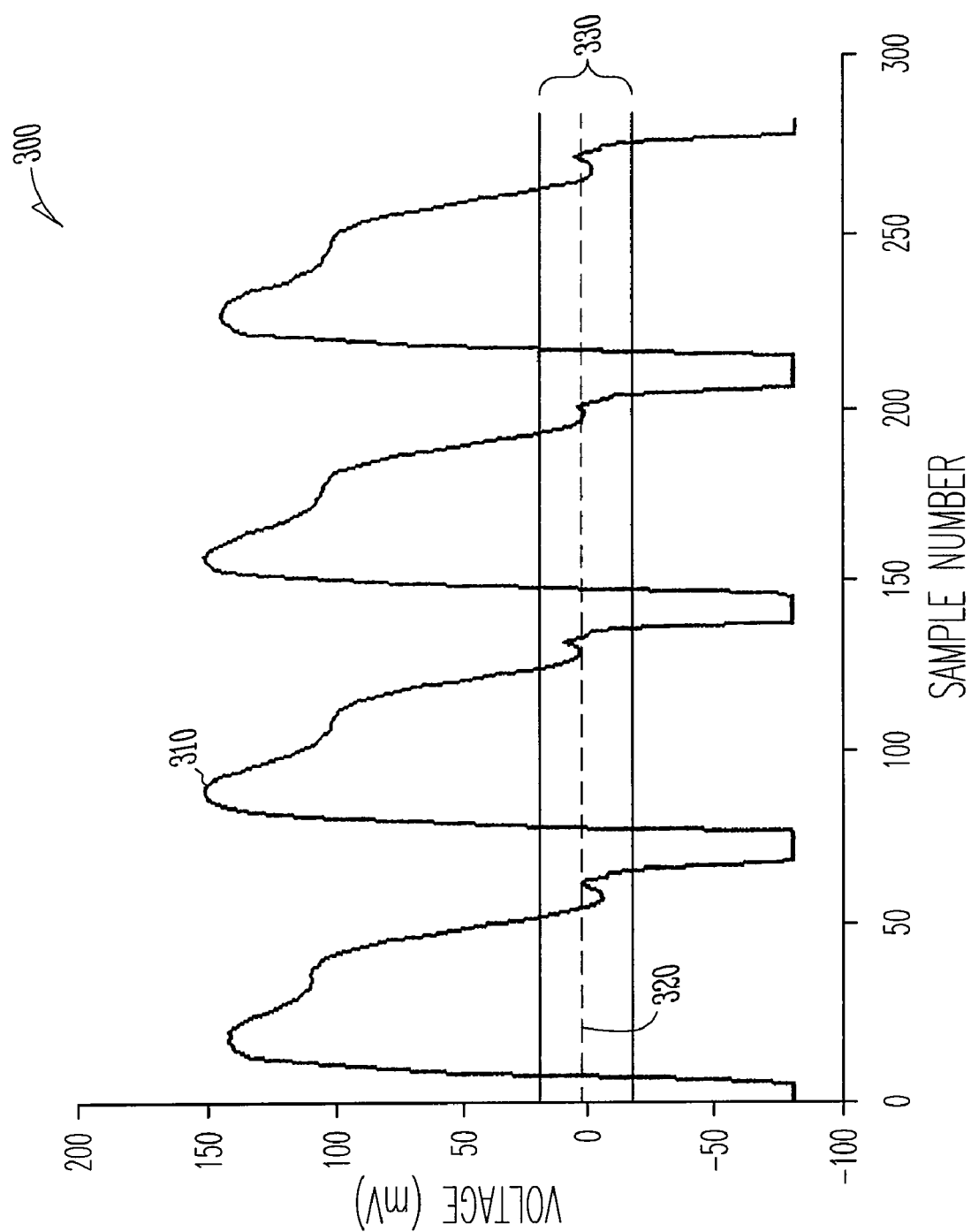
FIG. 3 is a graph showing a segment of a signal waveform of ventricular tachyarrhythmia that was not successfully converted to a normal heart rhythm using ATP.

FIG. 3 is a graph 300 showing a segment of a signal waveform 310 of ventricular tachyarrhythmia that was not successfully converted to a normal heart rhythm using ATP. The signal baseline 320 and the effective amplitude band 330 are indicated. When compared to FIG. 2, it can be seen that the signal waveform 310 shown in FIG. 3 spends more time outside of the amplitude band 330 than the signal waveform of FIG. 2. One potential explanation for the difference in signal morphology is that in a non-pace-terminable arrhythmia, the longer time spent outside of the amplitude band corresponds to cardiac cells spending a longer time in electrical saturation in which the cells are less responsive to ATP stimuli or other pacing voltage levels.

Figure 4:
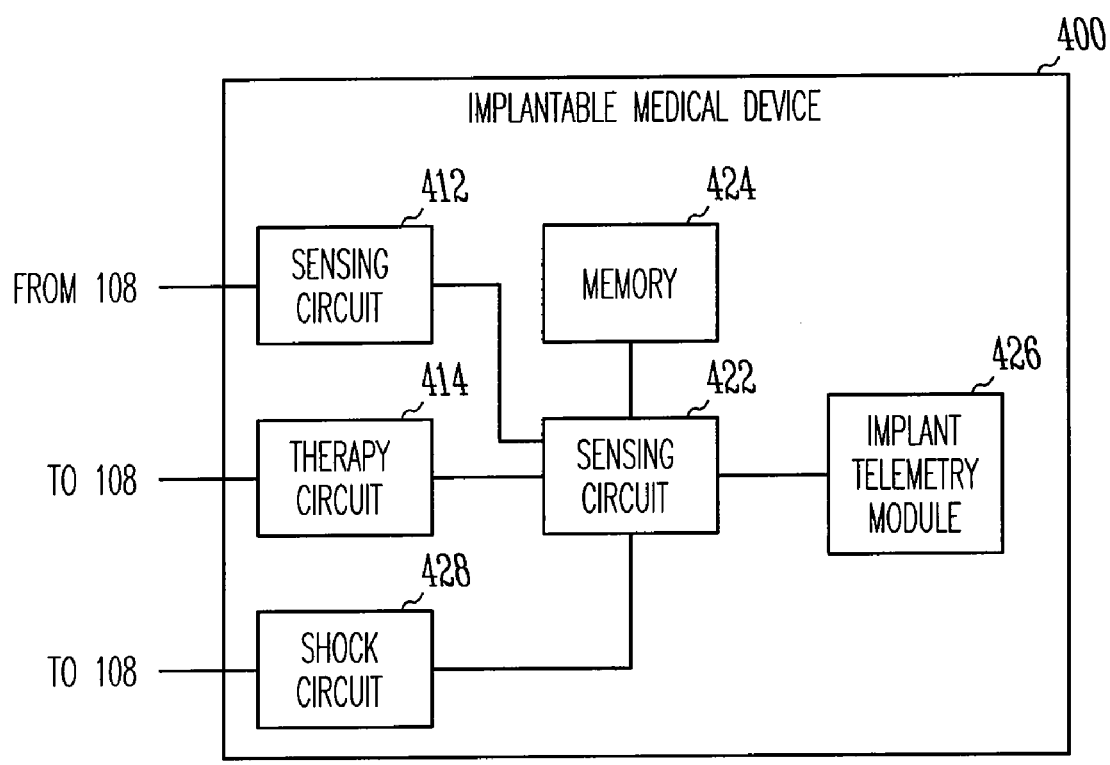
FIG. 4 is a block diagram of an implantable medical device used in a system used to treat cardiac arrhythmia.

FIG. 4 is a block diagram of portions of an IMD 400 used in a system used to treat cardiac arrhythmia. The IMD 400 includes a signal sensing circuit 412 to sense electrical activity signals of a heart on the lead or leads 108 and electrodes. To sense the electrical signals, the sensing circuit 412 typically includes sense amplifier circuits. The IMD 400 includes a pacing therapy circuit 414 to deliver electrical therapy to a heart through the lead or leads 108 and electrodes. The IMD 400 includes a controller circuit 422 coupled to the signal sensing circuit 412 and the therapy circuit 414. The controller circuit 422 is operable to detect a ventricular tachycardia heart rhythm from the heart signal, such as by executing an algorithm or algorithms implemented by hardware, software, firmware or any combination of hardware, software or firmware. The controller circuit 422 is further operable to then measure an amount of time the heart signal is outside of an effective amplitude band and initiate ATP therapy if the measured amount of time is less than a threshold amount of time. In one embodiment, an amount of time or a threshold amount of time refers to an absolute time measured in time units, such as fractions of seconds. In another embodiment, an amount of time or the threshold refers to a ratio comparing time outside of the band to the time inside of the band. For example, the amount of time is the ratio of the time spent outside the band to the time spent inside the band, or vice versa.

To determine an effective amplitude band, the IMD 400 further includes a sampling circuit coupled to the sensing circuit 412 and the controller circuit 422. The sampled values comprise an electrogram of the heart signal and are stored in a memory 424 coupled to the controller circuit 422. From the sampled heart signal, the controller circuit 422 determines a baseline signal value. In one embodiment, the controller circuit 422 is operable to select the baseline signal value using a segment of N ventricular depolarizations, where N is a positive integer. In one example of the embodiment, the N depolarizations include the most recently observed N ventricular depolarizations of the heart. The value of N implemented in an IMD 400 is function of the amount of memory available and the amount of processing time available to process a waveform signal. In one example, such as in the example signal waveforms of FIGS. 2 and 3, N is equal to four. However, N could be set to a different number.

In one embodiment of determining a signal baseline value, the controller circuit 422 selects the signal baseline value from a set of candidate baseline values. Each candidate baseline value corresponds to a DC voltage. The controller circuit 422 is operable to determine the number of times the heart signal crosses a candidate baseline value during the N depolarizations. The controller circuit 422 then takes the next candidate baseline value and determines the number of times the heart signal crosses the next candidate baseline value during the N depolarizations. The candidate baseline value that has the highest number of heart signal crossings is deemed the effective baseline signal value. The controller circuit 422 then uses the effect baseline and the amplitude of the heart signal to define the effective amplitude band as a fraction of the signal amplitude centered about the effective baseline value.

To determine the number of times the heart signal crosses a candidate baseline value, in another embodiment, the controller circuit 422 subtracts the candidate baseline value from the sampled values of the heart signal stored in memory 424. The number of times the heart signal crosses the candidate baseline value then corresponds to the number of changes in sign value in the resulting difference. If there is more than one candidate baseline value that has the highest number of signal crossings, the effective baseline value is computed using a central tendency of these candidate baseline values. In one embodiment, the central tendency is a mean value of the candidate baselines having the highest number of signal crossings.

Figure 5:
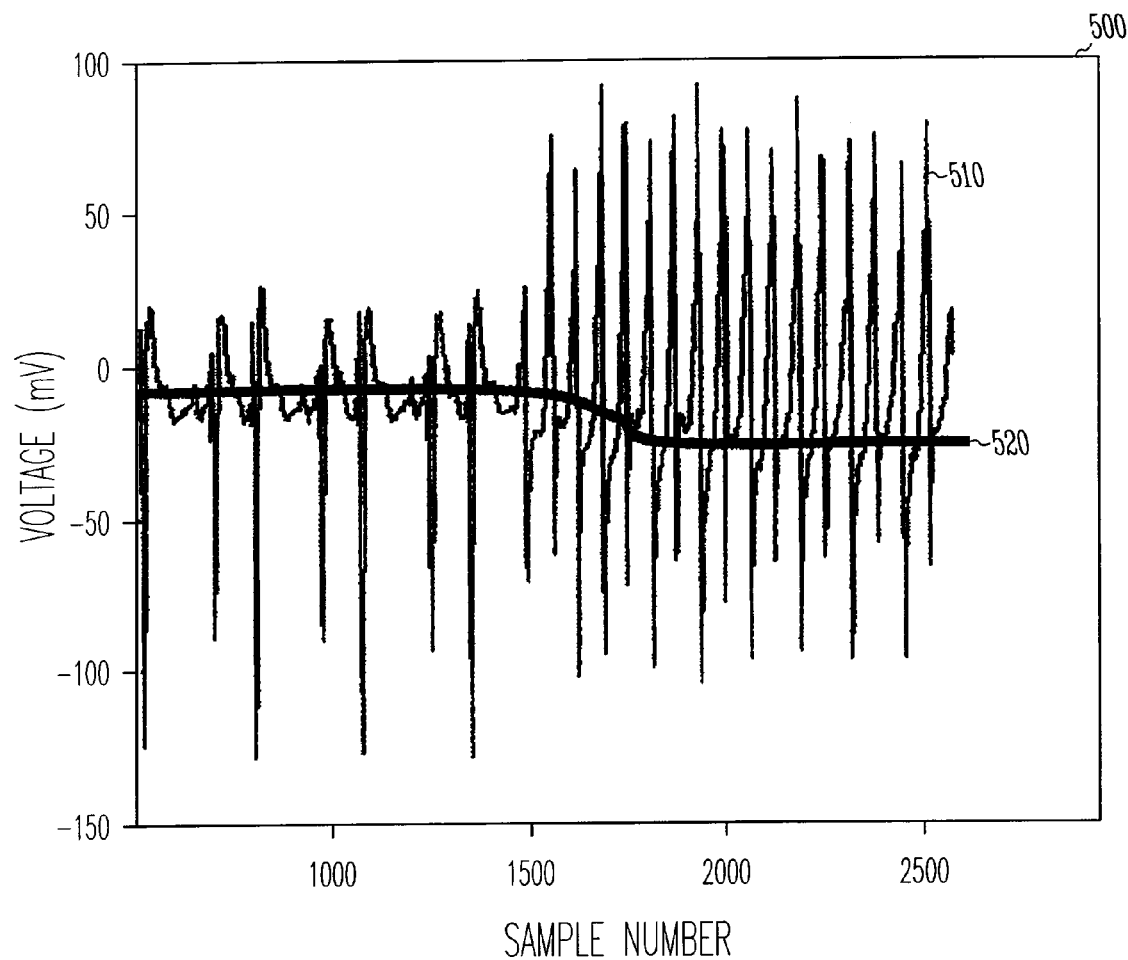
FIG. 5 is a graph of a heart signal waveform that transitions from normal rhythm into tachyarrhythmia.

FIG. 5 is a graph 500 of a heart signal waveform 510 that transitions from normal rhythm into tachyarrhythmia. The graph 500 shows how the effective baseline value 520 can shift during tachyarrhythmia. Thus the effective baseline and effective amplitude band should be computed from the heart signal waveform 520 during a detected tachyarrhythmia.

Returning to FIG. 4, another embodiment of the IMD 400 includes a defibrillation shock circuit 428 coupled to the controller circuit 422. In the embodiment, the controller circuit 422 is operable to initiate delivery of a defibrillation shock if the measured time that a heart signal is outside of an effective amplitude band is greater than a threshold time value. In one embodiment, the controller circuit 422 is further operable to initiate charging of the defibrillation therapy circuit in response to detecting a ventricular tachycardia heart rhythm and to delay the delivery of a defibrillation shock if the measured time is less than the threshold time value. In another embodiment, the controller circuit 422 is operable to delay delivery of a defibrillation shock until the measured time is greater than the threshold time value.

Further embodiments of the IMD 400 include using the above described morphology information in combination with one or more other predictors of pace-terminable arrhythmia. In one embodiment, the predictor is heart rate. In another embodiment the predictor is heart rate stability. In the embodiments, the controller circuit 422 is operable to measure the rate, or the stability, or both. A measurement of the time the heart signal is outside of the effective amplitude band is used in combination with the measured rate and/or stability to determine whether to initiate ATP therapy or defibrillation shock therapy. For example, if the measured stability is greater than twenty, the controller circuit 422 os operable to initiate delivery of defibrillation shock therapy instead of ATP therapy. In a further example, the multiple predictors are individually weighted to form a composite predictor of whether a particular arrhythmia is ATP-terminable.

When the morphology algorithm described above was applied to the developmental database, the morphology algorithm used alone yielded 64% sensitivity and 69% specificity. Sensitivity refers to the sensitivity of correctly identifying tachyarrhythmia episodes that that are non-pace terminable, and specificity refers to correctly identifying tachyarrhythmia episodes that are convertible to normal heart rhythm using ATP. This means that the morphology algorithm by itself correctly identified 64% of the non-pace terminable tachyarrhythmia episodes in the database and correctly identified 69% of the pace-terminable episodes. When the morphology algorithm was applied in combination with the above described rate and stability algorithm, the sensitivity improved to 78% sensitivity while specificity decreased to 64%.

Further embodiments of a system used to treat cardiac arrhythmia further comprise an external device to communicate with the IMD 400. In one embodiment, the external device is an IMD programmer and the IMD 400 communicates using telemetry module 426. In another embodiment, the external device is operable to communicate with a computer network, such as a hospital computer network (e.g. intranet) or the internet. In another embodiment, the external device includes a display to display patient information about those ventricular tachycardia episodes treated with ATP therapy and those episodes treated with a defibrillation shock. In one such embodiment, the external device is operable to receive patient information from the IMD 400 regarding sampled values of the heart signal, effective baseline value, and the effective amplitude band and to display the information. In another embodiment, the patient information includes a histogram of patient information about ventricular tachycardia episodes and whether they were treated with ATP therapy or a defibrillation shock.

Figure 6:
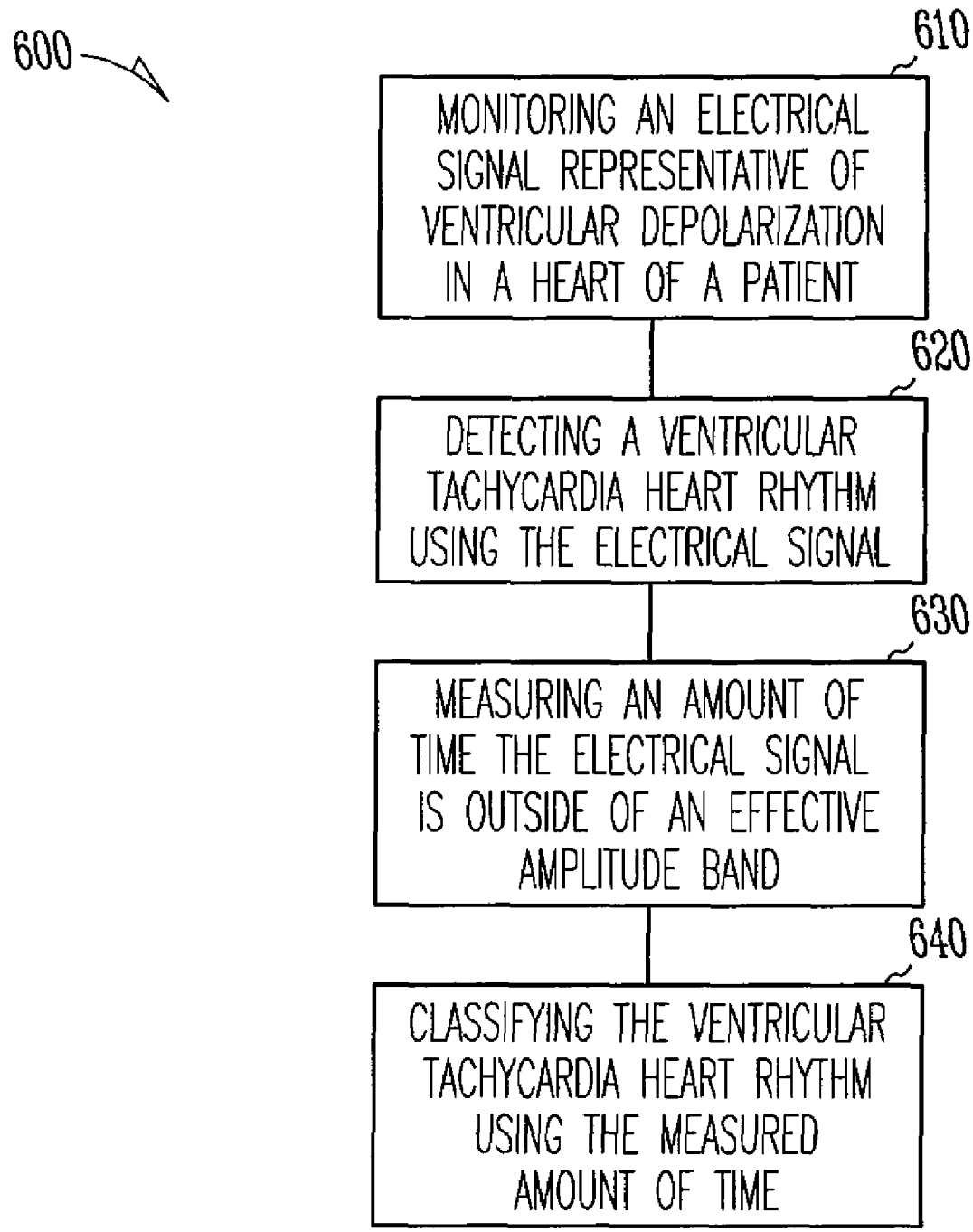
FIG. 6 shows a block diagram of a method for treating cardiac arrhythmia.

FIG. 6 shows a block diagram 600 of a method for treating cardiac arrhythmia. At 610, an electrical signal representative of ventricular depolarization in a heart of a patient is monitored. At 620, a ventricular tachycardia heart rhythm is detected using the electrical signal. At 630, an amount of time which the electrical signal is either outside or inside of an effective amplitude band is measured. At 640, the ventricular tachycardia heart rhythm is classified using the measured amount of time. In another embodiment, classifying the ventricular tachycardia heart rhythm includes deeming that the ventricular tachycardia heart rhythm is an anti-tachyarrhythmia pacing (ATP) terminable rhythm using the measured amount of time. For example, if the amount of time that an electrical signal is outside of an effective amplitude band exceeds a threshold value, the tachyarrhythmia is deemed non-ATP terminable. In one particular example, the effective amplitude band is 26% of the effective amplitude centered on the baseline, and the amount of time threshold value is one-third. In another particular example, the effective amplitude band is 16% of the effective amplitude and the amount of time threshold is one-half. Conversely, the classification can be done using the amount of time a signal spends within the effective amplitude band. In this case, if an amount of time which the electrical signal is inside of the effective amplitude band exceeds a threshold value, then the tachyarrhythmia is deemed ATP terminable.

In yet another embodiment of the method, deeming that the ventricular tachycardia heart rhythm is an ATP terminable rhythm using the measured amount of time includes comparing a fraction of time the electrical signal is outside of the effective amplitude band to a fraction threshold value, and deeming that the ventricular tachycardia heart rhythm is an ATP terminable rhythm if the fraction of time is less than the fraction threshold value. In one such embodiment, the fraction threshold value is determined using a patient population. In another such embodiment, the fraction threshold value is determined using a profile of the patient. In another embodiment, the method further includes providing ATP therapy if the tachycardia is deemed an ATP terminable rhythm, otherwise treating the tachycardia with a defibrillation shock.

The accompanying drawings that form a part hereof, show by way of illustration, and not of limitation, specific embodiments in which the subject matter may be practiced. The embodiments illustrated are described in sufficient detail to enable those skilled in the art to practice the teachings disclosed herein. Other embodiments may be utilized and derived therefrom, such that structural and logical substitutions and changes may be made without departing from the scope of this disclosure. This Detailed Description, therefore, is not to be taken in a limiting sense, and the scope of various embodiments is defined only by the appended claims, along with the full range of equivalents to which such claims are entitled.

Such embodiments of the inventive subject matter may be referred to herein, individually and/or collectively, by the term "invention" merely for convenience and without intending to voluntarily limit the scope of this application to any single invention or inventive concept if more than one is in fact disclosed. Thus, although specific embodiments have been illustrated and described herein, it should be appreciated that any arrangement calculated to achieve the same purpose may be substituted for the specific embodiments shown. This disclosure is intended to cover any and all adaptations, or variations, or combinations of various embodiments. Combinations of the above embodiments, and other embodiments not specifically described herein, will be apparent to those of skill in the art upon reviewing the above description.

The Abstract of the Disclosure is provided to comply with 37 C.F.R. §1.72(b), requiring an abstract that will allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separate embodiment.

What is claimed is:

1. A method of using an implantable medical device (IMD) comprising:
   monitoring an electrogram signal providing a voltage versus time representation of a ventricular depolarization voltage amplitude in a heart of a patient, the electrogram obtained using an implantable electrode disposed on or near the heart;
   determining, using the IMD during and for a particular tachyarrhythmia episode, a signal baseline value of the electrogram signal specific to that particular tachyarrhythmia episode and an effective amplitude band around the signal baseline value;
   detecting a ventricular tachycardia (VT) heart rhythm using the electrical signal;
   measuring an amount of time an amplitude of the electrogram signal is one of inside or outside of the effective amplitude band;
   classifying, using the measured amount of time, whether the VT heart rhythm is anti-tachyarrhythmia pacing (ATP) terminable or whether the VT heart rhythm instead requires a defibrillation shock; and
   providing ATP therapy if the tachycardia is deemed an ATP terminable rhythm, otherwise treating the tachycardia with a defibrillation shock.

2. The method of claim 1, wherein deeming that the ventricular tachycardia heart rhythm is an ATP terminable rhythm using the measured amount of time includes:
   comparing a fraction of time the electrogram signal is one of outside or inside of the effective amplitude band to a fraction threshold value; and
   deeming that the ventricular tachycardia heart rhythm is an ATP terminable rhythm if the fraction of time is less than the fraction threshold value when outside the effective amplitude band time is used, or the fraction of time is greater than the fraction threshold value when inside the effective amplitude band time is used.

3. The method of claim 2, wherein the fraction threshold value is determined using a patient population.

4. The method of claim 2, wherein the fraction threshold value is determined using a profile of the patient.

5. The method of claim 1, wherein deeming that the ventricular tachycardia heart rhythm is an ATP terminable rhythm using the measured amount of time includes using the measured amount of time the electrogram signal is outside of the effective amplitude band and monitoring ventricular rate, or ventricular rate stability, or both.

6. The method of claim 5, wherein monitoring ventricular rate stability includes deeming that defibrillation shock should be used instead of the ATP therapy if a ventricular rate is unstable.

7. The method of claim 1, wherein measuring an amount of time includes measuring an amount of time the electrogram signal is outside of the effective amplitude band.

8. The method of claim 7, wherein determining the signal baseline value and the effective amplitude band of the electrogram signal includes:
   selecting a first candidate baseline value using a signal segment of N depolarizations, where N is a positive integer;
   determining a first number of times the electrogram signal crosses the first candidate baseline value during the N depolarizations;
   selecting at least one additional candidate baseline value and determining at least one additional number of times the electrogram signal crosses the additional candidate baseline value during the N depolarizations;
   selecting the candidate baseline value that has a highest number of crossings of the electrogram signal as an effective baseline value; and
   defining the effective amplitude band as a fraction of the electrogram signal amplitude centered around the effective baseline value.

9. The method of claim 8, wherein the N depolarizations are the last N successive ventricular depolarizations.

10. The method of claim 8, wherein selecting at least one additional candidate baseline value includes selecting a plurality of additional candidate values, and wherein if multiple candidate baseline values have the highest number of crossings of the electrogram signal, the effective baseline value is computed using a central tendency of the candidate baseline values that have the highest number of crossings.

11. The method of claim 8, wherein the effective baseline value is a range of values.

12. The method of claim 8, wherein the fraction of the signal amplitude centered on the effective baseline value is about one-third of the peak-to-peak amplitude of the electrogram signal.

13. The method of claim 1, wherein detecting a ventricular tachycardia heart rhythm from the electrogram signal includes monitoring a ventricular rate.

14. A system, comprising:
   an implantable medical device (IMD) comprising:
      a ventricular heart signal sensing circuit to produce an electrogram signal, providing a voltage versus time representation of a ventricular depolarization voltage amplitude in a heart of a patient; and
      a controller circuit coupled to the signal sensing circuit, wherein the controller circuit is configured to:
         detect a ventricular tachycardia heart rhythm from the electrogram signal;
         determine, during and for a particular tachyarrhythmia episode, a signal baseline value of the electrogram signal specific to that particular tachyarrhythmia episode and an effective amplitude band around the signal baseline value;
         measure an amount of time the electrogram signal is one of inside or outside of the effective amplitude band;
         classify whether the ventricular tachycardia heart rhythm is anti-tachyarrhythmia pacing (ATP) terminable or whether the VT heart rhythm instead requires a defibrillation shock using the measured amount of time; and a pacing therapy circuit, coupled to the controller circuit, and configured to provide ATP therapy if the tachycardia is deemed an ATP terminable rhythm, and a defibrillation shock circuit, coupled to the controller circuit, and configured to otherwise treat the tachycardia with a defibrillation shock.

15. The system of claim 14, wherein the controller circuit is configured to initiate delivery of a defibrillation shock if the measured amount of time the electrogram signal is outside of the effective amplitude band is greater than a threshold amount of time.

16. The system of claim 15, wherein the controller circuit is further configured to initiate charging of the defibrillation shock circuit in response to detecting a ventricular tachycardia heart rhythm and to delay the delivery of a defibrillation shock if the measured amount of time is less than the threshold amount of time.

17. The system of 15, wherein the controller circuit is configured to measure ventricular rate stability and to initiate the ATP therapy using the measured ventricular rate stability and the measured amount of time the electrogram signal is outside of the effective amplitude band.

18. The system of claim 17, wherein the controller circuit is configured to initiate the delivery of the defibrillation shock instead of the ATP therapy if the ventricular rate is unstable.

19. The system of claim 14, wherein the system further comprises an external device to communicate with the IMD, wherein the external device includes a display to display patient information about ventricular tachycardia episodes treated with the ATP therapy and about ventricular tachycardia episodes treated with a defibrillation shock.

20. The system of claim 19, wherein the patient information includes a histogram of patient information about ventricular tachycardia episodes and whether they were treated with the ATP therapy or a defibrillation shock.

21. The system of claim 19, wherein the external device is configured to communicate with a computer network.

22. The system of claim 14, wherein the IMD further comprises:
a sampling circuit coupled to the ventricular heart signal sensing circuit and controller circuit; and
a memory coupled to the controller circuit to store sampled values of the electrogram signal, and wherein the controller circuit is further configured to:
select a candidate for a baseline value using N depolarizations;
determine a first number of times the electrogram signal crosses the candidate baseline value during the N depolarizations;
select at least one additional candidate baseline value and determine a second number of times the electrogram signal crosses the additional candidate baseline value during the N depolarizations;
select the candidate baseline value that has a highest number of crossings of the electrogram signal as an effective baseline value; and
define the effective amplitude band as a fraction of the electrogram signal amplitude centered on the effective baseline value.

23. The system of claim 22, wherein the controller circuit is further configured to:
subtract the candidate baseline value from the sampled values of the electrogram signal; and
determine the number of times the electrogram signal crosses the candidate baseline value using the number of changes in sign value in the result of the subtraction.

24. The system of claim 22, wherein the controller circuit is configured to define the effective amplitude band using the last N successive ventricular depolarizations.

25. The system of claim 22, wherein an external device is configured to receive patient information from the IMD regarding sampled values of the electrogram signal, effective baseline value, and the effective amplitude band and wherein the external device is further configured to display the information.

26. The system of claim 14, wherein the controller circuit is configured to initiate the ATP therapy if the measured amount of time that the electrogram signal is outside of the effective amplitude band is less than a first threshold amount of time or if the measured amount of time that the electrogram signal is inside of the effective amplitude band is greater than a second threshold amount of time.

27. A system, comprising:
an implantable medical device (IMD) comprising:
a ventricular heart signal sensing circuit to produce an electrogram signal providing a voltage versus time representation of a ventricular depolarization voltage amplitude in a heart of a patient;
a pacing therapy circuit; a defibrillation shock therapy circuit; and
a controller circuit coupled to the ventricular heart signal sensing circuit and the pacing therapy circuit, wherein the controller circuit is configured to:
detect a ventricular tachycardia heart rhythm from the electrogram signal;
determine, using implantable medical device during and for a particular tachyarrhythmia episode, a signal baseline value of the electrogram signal specific to that particular tachyarrhythmia episode and an effective amplitude band around the signal baseline value;
measure an amount of time an amplitude of the electrogram signal is inside of the effective amplitude band;
initiate anti-tachyarrhythmia pacing (ATP) therapy if the measured amount of time is greater than or equal to a threshold amount of time; and
otherwise, enable defibrillation shock therapy.

28. The system of claim 27, wherein the controller circuit is further configured to measure ventricular rate stability, and to initiate the ATP therapy using the measured ventricular rate stability and the measured amount of time the electrogram signal is inside of the effective amplitude band.

29. A system comprising:
an implantable medical device (IMD) comprising:
a ventricular heart signal sensing circuit to produce an electrogram signal providing a voltage versus time representation of a ventricular depolarization voltage amplitude in a heart of a patient;
a pacing therapy circuit;
a defibrillation shock therapy circuit; and
a controller circuit coupled to the ventricular heart signal sensing circuit the pacing therapy circuit, and the defibrillation shock therapy circuit, wherein the controller circuit is configured to:
detect a ventricular tachycardia heart rhythm from the electrogram signal;
measure an amount of time an amplitude of the electrogram signal is outside of an effective amplitude band that is substantially centered on an established baseline value of the electrogram signal;
enable anti-tachyarrhythmia pacing (ATP) therapy if the measured amount of time is less than a threshold amount of time; and
otherwise, enable defibrillation shock therapy.

30. The system of claim 29, wherein the controller circuit is further configured to measure ventricular rate stability, and to initiate the ATP therapy using the measured ventricular rate stability and the measured amount of time the electrogram signal is outside of the effective amplitude band.

31. A system, comprising:
an implantable medical device (IMD) comprising:
a ventricular heart signal sensing circuit to produce an electrogram signal providing a voltage versus time representation of a ventricular depolarization voltage amplitude in a heart of a patient;
a pacing therapy circuit;
a defibrillation shock therapy circuit; and
means for:
detecting a ventricular tachycardia heart rhythm from the electrogram signal;
determining, during and for a particular tachyarrhythmia episode, a signal baseline value of the electrogram signal specific to that particular tachyarrhythmia episode and an effective amplitude band around the signal baseline value;
measuring an amount of time an amplitude of the electrogram signal is one of inside or outside of the effective amplitude band;
classifying whether the ventricular tachycardia heart rhythm is anti-tachyarrhythmia pacing (ATP) terminable or whether the ventricular tachycardia heart rhythm instead requires a defibrillation shock using the measured amount of time; and
enabling at least one of anti-tachyarrhythmia pacing (ATP) therapy and
defibrillation shock therapy using the classification.

32. An implantable medical device comprising:
means for monitoring an electrogram signal providing a voltage versus time representation of a ventricular depolarization voltage amplitude in a heart of a patient;
means for detecting a ventricular tachycardia heart rhythm using the electrogram signal;
means for determining, using the implantable medical device during and for a particular tachyarrhythmia episode, a signal baseline value of the electrogram signal specific to that particular tachyarrhythmia episode and an effective amplitude band around the signal baseline value;
means for measuring an amount of time an amplitude of the electrogram signal is one of inside or outside of an effective amplitude band;
means for classifying whether the ventricular tachycardia heart rhythm is anti-tachyarrhythmia pacing (ATP) terminable or whether the ventricular heart rhythm instead requires a defibrillation shock using the measured amount of time; and
means for providing ATP therapy if the tachycardia is deemed an ATP terminable rhythm, and for otherwise treating the tachycardia with a defibrillation shock.

33. A method of using an implantable medical device comprising:
monitoring an electrogram signal providing a voltage versus time representation of a ventricular depolarization voltage amplitude in a heart of a patient;
detecting a ventricular tachycardia heart rhythm using the electrogram signal;
measuring an amount of time an amplitude of the electrogram signal is outside of an effective amplitude band that is substantially centered on a baseline value of the electrogram signal;
classifying the ventricular tachycardia heart rhythm using the measured amount of time, including determining, using the measured amount of time, whether the ventricular tachycardia heart rhythm is anti-tachyarrhythmia pacing (ATP) terminable or whether the ventricular heart rhythm instead requires a defibrillation shock; and
providing ATP therapy if the tachycardia is deemed an ATP terminable rhythm, otherwise treating the tachycardia with a defibrillation shock.

34. The method of claim 33, wherein deeming that the ventricular tachycardia heart rhythm is an ATP terminable rhythm using the measured amount of time includes using the measured amount of time the electrogram signal is outside of the effective amplitude band and monitoring the ventricular rate or ventricular rate stability, or both.

35. The method of claim 34, wherein determining the effective amplitude band of the electrogram signal includes:
selecting a first candidate baseline value using a signal segment of N depolarizations, where N is a positive integer;
determining a first number of times the electrogram signal crosses the first candidate baseline value during the N depolarizations;
selecting at least one additional candidate baseline value and determining at least one additional number of times the electrogram signal crosses the additional candidate baseline value during the N depolarizations;
selecting the candidate baseline value that has a highest number of crossings of the electrical signal as an effective baseline value; and
defining the effective amplitude band as a fraction of the electrogram signal amplitude centered around the effective baseline value.

36. The method of claim 35, wherein the N depolarizations are the last N successive ventricular depolarizations.

37. A system, comprising:
an implantable medical device (IMD) comprising:
a ventricular heart signal sensing circuit to produce an electrogram signal providing a voltage versus time representation of a ventricular depolarization voltage amplitude in a heart of a patient;
a pacing therapy circuit;
a defibrillation shock therapy circuit; and
a controller circuit coupled to the ventricular heart signal sensing circuit, the pacing therapy circuit, and the defibrillation shock therapy circuit, wherein the controller circuit is configured to:
detect a ventricular tachycardia heart rhythm from the electrogram signal;
measure an amount of time an amplitude of the electrogram signal is outside of the effective amplitude band that is substantially centered on an established baseline value of the electrogram signal;
classify whether the ventricular tachycardia heart rhythm is anti-tachyarrhythmia pacing (ATP) terminable or whether the ventricular heart rhythm instead requires a defibrillation shock using the measured amount of time; and
wherein the pacing therapy circuit is configured to provide ATP therapy if the tachycardia is deemed an ATP terminable rhythm, the defibrillation shock therapy circuit configured to otherwise treat the tachycardia with a defibrillation shock.

38. The system of claim 37, wherein the controller circuit is configured to measure ventricular rate stability and to initiate the ATP therapy using the measured ventricular rate stability and the measured amount of time the electrogram signal is outside of the effective amplitude band.

39. The system of claim 37, wherein the system further comprises an external device to communicate with the IMD, wherein the external device includes a display to display patient information about ventricular tachycardia episodes treated with the ATP therapy and about ventricular tachycardia episodes treated with a defibrillation shock.

40. The system of claim 39, wherein the patient information includes a histogram of patient information about ventricular tachycardia episodes and whether they were treated with the ATP therapy or a defibrillation shock.

41. The system of claim 37, wherein the IMD further comprises:
- a sampling circuit coupled to the ventricular heart signal sensing circuit and controller circuit; and
- a memory coupled to the controller circuit to store sampled values of the electrogram signal, and wherein the controller circuit is further configured to:

select a candidate for a baseline value using N depolarizations;

determine a first number of times the electrogram signal crosses the candidate baseline value during the N depolarizations;

select at least one additional candidate baseline value and determine a second number of times the electrogram signal crosses the additional candidate baseline value during the N depolarizations;

select the candidate baseline value that has a highest number of crossings of the electrogram signal as an effective baseline value; and define the effective amplitude band as a fraction of the signal amplitude centered on the effective baseline value.

* * * * *